United States Patent [19]
Eck

[11] Patent Number: 5,043,448
[45] Date of Patent: Aug. 27, 1991

[54] ASYMMETRIC SYNTHESIS OF FURO(3,4-C) PYRIDINE DERIVATIVES

[75] Inventor: Charles Eck, Shrewsbury, Mass.

[73] Assignee: Societe de Conseils de Recherches et d'Applications Scientifiques, France

[21] Appl. No.: 557,975

[22] Filed: Jul. 26, 1990

[30] Foreign Application Priority Data

Jul. 27, 1989 [GB] United Kingdom ................ 8917168

[51] Int. Cl.[5] ........................................ C07D 491/048
[52] U.S. Cl. .................................. 546/116; 435/119
[58] Field of Search ........................................ 546/116

[56] References Cited

U.S. PATENT DOCUMENTS 4,383,998 5/1983 Esanu ................................ 546/116

FOREIGN PATENT DOCUMENTS 0337858 10/1989 European Pat. Off. .

OTHER PUBLICATIONS

Schoeffter et al., Eur. J. of Pharmacology, 136, pp. 235-237 (1987).

*Primary Examiner*—Bernard Dentz
*Attorney, Agent, or Firm*—Lucas & Just

[57] ABSTRACT

The invention relates to a method for the preparation of a non-racemic furo [3,4-c] pyridine derivatives of the formula I

I wherein $R_1$, $R_2$ and $R_3$ stand for various substitutents, comprising adding a concentrated strong acid to a solution of a non-racemic compound of the formula II

II in an amount sufficient to catalyze a deprotection/cyclodehydration. These compounds are known antihypertensives.

10 Claims, No Drawings

ASYMMETRIC SYNTHESIS OF FURO(3,4-C) PYRIDINE DERIVATIVES

The invention relates to a method for the preparation of non-racemic furo [3, 4-c] pyridine derivatives.

In this Specification the term "non-racemic" is used to indicate a single enantiomer or an enantiomer mixture in which one enantiomer predominates.

It is now generally recognized that two enantiomers of a drug molecule, when introduced into a biological environment, behave as if they were different chemical entities. These variations can be demonstrated as differences in:

1. protein binding,
2. metabolism,
3. pharmacokinetics,
4. tissue distribution,
5. receptor binding, and
6. enzyme inhibition;

and are caused by a difference in stereoconfiguration. The two enantiomers are generally labelled as R or S or (−) or (+) to distinguish them.

Thus, in vivo, any racemic mixture is constantly subjected to stereodifferentiation by encountering chiral surroundings either in solution or when bound to solid phase structures (cell receptors, etc). As a result of this stereodifferentiation, enantiomers may not only differ in therapeutic activity, but may behave antagonistically.

Consequently, it is becoming increasingly necessary for regulatory approval to provide toxicity, pharmacology, disposition and activity data for each individual isomer as well as the drug racemate (i.e., a 1:1 mixture of stereoisomers). This necessitates that methods be available for the generation of the optically pure drug enantiomers. Generally, three strategies can be employed to prepare pure isomeric products:

1. preparation of a racemate of the desired compound and separation of the racemate into its enantiomers;
2. preparation of a racemate of the desired compound, conversion of the racemate into a racemic derivative, separation of the racemic derivative into its enantiomers, and reconversion of each enantiomer separately into an enantiomer of the desired compound; and
3. asymmetric synthesis of individual enantiomers of the desired compound.

In typical organic synthesis, enantiomeric products are obtained without control over the ratio of one type of stereoisomer to the other and statistically these different enantiomers are obtained in a proportion of 1:1 to form a racemic mixture.

The invention is most particularly concerned with the conversion of a non-racemic compound of the general formula II

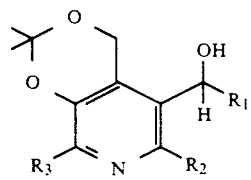

wherein $R_1$ represents a straight chain saturated or unsaturated hydrocarbon group having from 1 to 5 carbon atoms, a heterocyclic group having up to 6 ring atoms, a carbomonocyclic group, a phenyl group, a phenylalkyl group or a phenylalkenyl group, each of said groups being optionally substituted by one or more halogen atoms, trifluoromethyl groups, alkyl groups having from 1 to 5 carbon atoms, alkoxy groups having from 1 to 5 carbon atoms, alkylthio groups having from 1 to 5 carbon atoms, dialkylamine groups in which each of the two alkyl groups has from 1 to 5 carbon atoms, dialkylaminoalkoxy groups in which each of the two alkyl groups and the alkoxy group has from 1 to 5 carbon atoms or an α- or β-alkoxy-N-pyrrolidinyl group in which the alkoxy group has from 1 to 5 carbon atoms;

$R_2$ represents a hydrogen or halogen atom; and $R_3$ represents a straight chain or branched chain alkyl or alkenyl group having up to 6 carbon atoms, optionally substituted by a hydroxy, cyano, amino or substituted amino group or by an alkyl or alkenyl group having up to 4 carbon atoms to the corresponding non-racemic furo [3,4-c] pyridine derivative of the general formula I

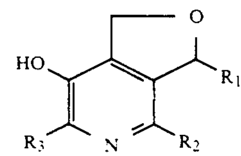

wherein $R_1$, $R_2$ and $R_3$ are as above defined.

A route is known for such a conversion, but is laborious, involving five steps as shown in the following reaction scheme:

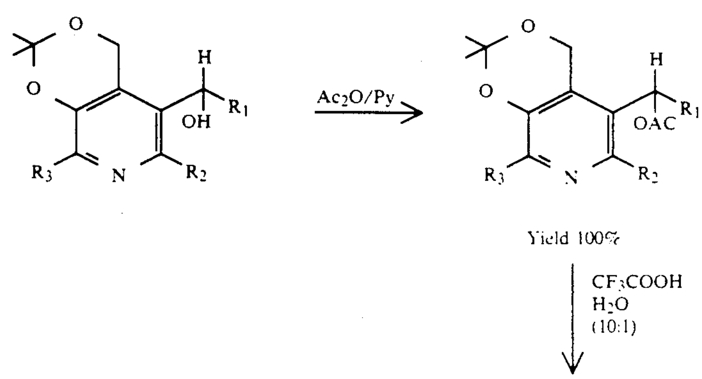

-continued

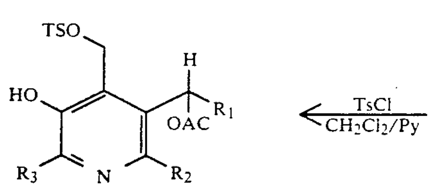

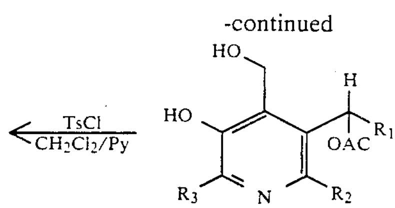

Yield 70% Yield 90%

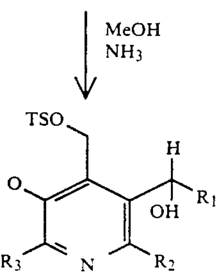

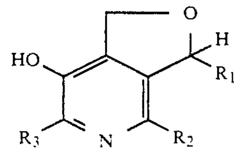

Yield 100% Yield 70%

The hydroxy group must first be protected. The acetonide blocking group can then be removed, and the resulting 4-hydroxymethyl group is then tosylated to provide for easier SN2 displacement subsequently. The acetoxy protecting group is then removed, and a base catalysed cyclisation provides the desired compound.

The invention provides a method for conversion of a non-racemic compound of the general formula II as herein defined to the corresponding non-racemic furo [3,4-c] pyridine derivative of the general formula I as herein defined, the method comprising adding a concentrated strong acid to a solution of the compound II in an amount sufficient to catalyse a deprotection/cyclodehydration reaction. There is thus achieved in a single step that which hitherto necessitated five steps.

Preferably the non-racemic compound II is dissolved in a solvent which forms an azeotrope with water. From a variety of such solvents, there may be mentioned benzene, toluene, ethyl acetate and chloroform.

The concentrated strong acid may be hydrochloric acid, sulphuric acid, perchloric acid or trifluoroacetic acid.

In a preferred embodiment, the starting material II is initially purified by alcohol or ethyl acetate crystallization before being dissolved in the solvent. When the starting material of the general formula II is optically enriched, i.e., 80/20, ethyl acetate crystallization may provide a product that is typically greater than 95% optically pure.

The non-racemic furo [3,4-c] pyridine derivative may be recovered by decanting the excess solution, including the unreacted compound of the general formula II, from a residue produced by the cyclodehydration reaction, dissolving the residue in alcohol to produce a mixture, determining what part of the alcohol mixture is a compound of the general formula I, and isolating the same from the alcohol mixture.

The non-racemic compound II which is the starting material for the method of the invention may be obtained from the corresponding racemic compound by oxidation to a ketone of the general formula III

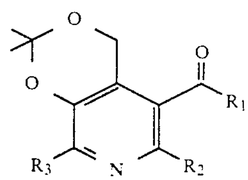

III wherein $R_1$, $R_2$ and $R_3$ are as defined hereinabove, followed by stereospecific reduction of the ketone. In detail, this method may comprise:

(a) dissolving the racemic form of the compound of the general formula II in an organic solvent to form a solution;

(b) adding dropwise an oxidizing agent to said solution in a sufficient amount to completely react with all the compound racemates of the general formula II;

(c) quenching the excess oxidizing agent with an alcohol;

(d) cooling the liquid to produce a solid compound precipitate;

(e) dissolving said solid crystals in tetrahydrofuran to form a mixture;

(f) adding to said mixture a chiral reducing agent to reduce said solid compound to the desired non-racemic compound of the general formula II and (g) isolating the non-racemic compound of the general formula II and dissolving it in a solvent.

The organic solvent may be acetone. A suitable oxidizing agent is Jones Reagent ($CrO_3H_2/H_2SO_4/H_2O$). The alcohol used in quenching is suitably isopropanol.

The initial stereocontrolled step of adding a hydride from a chiral metal hydride or borohydride reagents to acyclic ketones has been widely used for the preparation of optically active secondary alcohols, see for example, Brown, H. C., et al., *J. Org. Chem*, 52: 5406-12 (1987).

The chiral reducing agent may be N,B-Enantride TM (Aldrich Chemical Co ) or $MDBH_2$ (Expansia, European patent No. 0 061 408) in tetrahydrofuran (THF). Such reducing agents are produced by chiral modifications of complex metal hydrides as well as borohydrides (Brown, H. C., et al., *J. Org. Chem.*, 52: 5406-12 (1987).

N,B-Enantride TM is lithium hydrido (9-BBN-nopol-benzyl ether adduct), in a 0.5 m solution in THF. The following reagents are all suitable for use in the present invention: B-Ipc-9-BBN (Alpine borane, Aldrich), N,B-Entrane (Aldrich), $Ipc_2BCl$ (Aldrich), $BM_3$-ANDPB (2:1) (see S. Itsuno, J. Chem. Soc., Chem. Comm.1981, 315), (R,R)-2,5-dimethylborolane (see S. Masamune, J. Am Chem. Soc. 1986, 108, 7402), N,B-Enantride (Aldrich), $LiBH_4$-DBC-t- BuOH (see K. Soal, J. Chem. Soc., Chem. Com. 1984, 413), $NaBH_4$-IBA-DIPGF (see S. Itsuno, J. Chem. Soc., Perkin Trans. 1, 1981, 900), K-Glucoride (see H. C. Brown, J. Org. Chem. 1986, 51, 1934), $LiAlH_4$-Darvon Alc (see H. Mosher, J. Am. Chem. Soc.,1972, 94, 9254) $LiAlH_4$-MEP-ArOH (see J. P. Vigneron, Tetrahedron 1976, 32, 939), $LiAlH_4$-Diamine (see M. Asami, Heterocycles, 1979, 12, 499), $LiAlH_4$-Aminobutanol (see T. Sato, Tet. Letters 1982, 23, 4111), Binal H (See R. Noyori, J. Am. Chem. Soc. 1979, 101, 3129), $LiAlH_4$-DBP-EtOH (see K. Yamamoto, J. Chem. Soc., Chem. Comm. 1984, 1490),$LiAlH_4$-MEP-NEA (see K. J. Koga, J. Chem. Soc., Chem. Comm.1980,1026), $LiAlH_4$-MEP-EAP (see S. Terashima, Chem. Letters 1984, 239), TBADH (*Thermoanaerobium brockii* alcohol dehydrogenase, Sigma Chem.Co.)

The non-racemic compound II may alternatively be obtained from the ketone III by dissolving it in a vigorously stirred fermenting slurry of yeast, water and a carbohydrate;

(b) adding additional carbohydrate and yeast to provide continued vigorous fermentation to form the desired chiral compound of the general formula II;

(c) continuing said fermentation until formation of the compound of the general formula II ceases and (d) isolating the compound of the general formula II.

The following Examples describe the preparation of the ketone III: $R_1$=4-chlorophenyl, $R_2$=H, $R_3$=$CH_3$ from the corresponding racemic alcohol II (Example 1), the preparation of the corresponding non-racemic alcohol II from the ketone III (Example 2), and the preparation of the corresponding non-racemic furo [3,4-c] pyridine derivative I: $R_1$=4-chlorophenyl, $R_2$=H, $R_3$=$CH_3$ from the non-racemic alcohol II by the method of the invention.

EXAMPLE 1

Synthesis of ketone III by oxidation of racemic 2,2,8-trimethyl-5-(4-chloro-α-hydroxybenzyl)-pyrido-[4,3-e]-1,3-Dioxane 2.16 g (6,7 mmoles) of racemic 2,2,8-trimethyl-5-(4-chloro -α-hydroxybenzyl)-pyrido- [4,3-e]-1,3-dioxane were poured into an Erlenmeyer flask and dissolved in 150 ml acetone. Jones reagent ($CrO_3/H_2SO_4/H_2O$) was added dropwise to the stirred solution until the starting material was completely used up as determined by TLC (thin layer chromatography). Excess oxidizing agent was quenched in isopropanol. The reaction mixture was poured into iced water and the solid that formed was removed by filtration. The reaction mixture was washed several times with water. The crude product was dissolved in methanol and set aside to crystallize. Two crops of plate-like crystals were collected (1.7 g) and thoroughly dried under nitrogen. The final product was homogeneous by TLC (dichloromethane: methanol, 10:1 by volume, Rf=0.8) and HPLC.

EXAMPLE 2

Synthesis of (+) -2, 2, 8-trimethyl-5-(4-chloro-α-hydroxy-benzyl)-pyrido-[4,3-e]-1,3-dioxane 1.1 g (3.5 mmol) of the ketone prepared in Example 1 were poured into a 50 ml round bottomed flask and dissolved in 35 ml of dry THF (tetrahydrofuran). The flask was sealed with a septum, placed under a nitrogen atmosphere and set into a dry ice/acetone bath. [1S]-N,B-Enantride TM (13.3 ml, 6,65 mmoles) was then added in one portion and the rate of reduction was followed by HPLC (high pressure liquid chromatography) at T - 0, T - 1 hr and T - 2 hr. Typically, most of the ketone was reduced to (+)-2,2,8-trimethyl-5(4-chloro-α-hydroxybenzyl)-pyrido-[4,3-e]-1,3-dioxane after two hours. The reaction mixture was evaporated to dryness on a roto-vac, the residue was redissolved in dichloromethane, loaded on the top of a silica gel column (42 g) and eluted with dichloromethane. The separation was assayed by TLC and fractions numbers 131–160 were combined. The solvent was removed by rotary evaporation and the residue (1.05 g) was redissolved in 12 ml of ethyl acetate. On cooling, a fluffy white crop of crystals precipitated and was collected (0.25 g). This sample was homogeneous by TLC (dichloromethane:methanol, 10:1 by volume) and HPLC and provided (+)-2,2,8-trimethyl-5-(4-chloro-α-hydroxybenzyl)-pyrido-[4,3-e]-1,3-dioxane of high enantiomeric enrichment (>86%).

EXAMPLE 3

Deprotection/cyclodehydration of (+)-2,2,8-trimethyl-5-(4-chloro-α-hydroxybenzyl)-pyrido-[4,3-e]-1,3-dioxane to (+)-3-(4-chlorophenyl)-1,3-dihydro-7-hydroxy-6-methylfuro[3,4-c-pyridine 317 mg (1 mmol) of (+)-2,2,8-trimethyl-5-(4-chloro-α- hydroxybenzyl)-pyrido-[4,3-e]-1,3-dioxane, prepared as described in Example 2, were poured into 100 ml round bottomed flask and dissolved in 60 ml of benzene. Two drops of concentrated sulphuric acid were added, a Dean-Stark adaptor was attached and the reaction mixture was refluxed for two hours. The benzene solution (which contained unreacted starting material) was poured off from the yellow green solid which had formed on the bottom of the flask. The insoluble material was dissolved in methanol, spotted onto a 2000μ silica gel TLC plate and eluted with dichloromethane: methanol, 7:1 by volume.

The major U.V. visible band which co-eluted with a spot of known (+)-3-(4-chlorophenyl)-1,3-dihydro-7-hydroxy-6-methyl -furo-[3,4-c]-pyridine was excised from the plate and the organic material from the silica was washed with methanol. Removal of the methanol by rotary evaporation gave a solid product shown to be (+)-3-(4-chlorophenyl)-1,3-dihydro-7- hydroxy-6-methylfuro-[3,4-c]-pyridine by spectroscopic and chromatographic comparison with an authentic sample.

Chiral phase HPLC of the isolated product showed it to be a mixture of (−) and (+)-3-(4-chlorophenyl)-1,3-dihydro-7-hydroxy-6-methylfuro- [3,4-c]pyridine in a ratio that is identical to that of the starting (+)-2,2,8-trimethyl-5-(4-chloro-α-hydroxybenzyl)-pyrido-[4,3-e]-1,3-dioxane.

The furo [3,4-c]pyridine derivative compounds obtained according to this invention are of use in the various pharmaceutical fields described in U.S. Pat. Nos. 4,383,998, 4,581,363, 4,585,776, 4,569,939, 4,581,362 and 4,659,719. Accordingly, this invention also relates to therapeutic compositions, one active ingredient in which is an enantiomer or a mixture of enantiomers wherein one enantiomer is substantially predominant.

The appropriate administration modes are described in the above mentioned patents, but the dosage required is lower due to the enhanced activity of the selected enantiomer or of the enantiomer mixtures wherein said enantiomer is predominant.

PRESENTATION

The preferred administration mode is tablets and capsules. For tablets, each dosage unit contains from 5 to 100 mg or, preferably, 10 to 25 mg of the active principle associated with an appropriate inert carrier, such as starch.

POSOLOGY

In human therapy, the doses to be used are from 50 to 150 mg/day for at least one week, and preferably for longer periods of time.

What is claimed is:

1. A method of producing, in non-racemic form (that is as a single enantiomer or as an enantiomeric mixture in which one enantiomer predominates), a compound of the formula I:

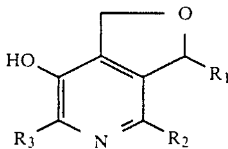

I wherein $R_1$ is selected from the group consisting of a) a straight chain saturated hydrocarbon groups having from 1 to 5 carbon atoms, b) a straight chain unsaturated hydrocarbon group having from 1 to 5 carbon atoms, c) a heterocyclic group having up to 6 ring atoms, d) a carbomonocyclic group, e) a phenyl group, f) a phenylalkyl group, and g) a phenylalkenyl group, each of said groups a to g being optionally substituted with one or more substituents selected from the group consisting of halogen atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms and α- or β-alkoxy-N-pyrrolidinyl groups in which the alkoxy group has from 1 to 5 carbon atoms;

$R_2$ is selected from a hydrogen atom and a halogen atom; and $R_3$ is selected from the group consisting of straight chain and branched chain alkyl and alkenyl groups having up to 6 carbon atoms, optionally substituted by a substituent selected from the group consisting of hydroxy, cyano, amino groups, substituted amino groups, alkyl groups having up to 4 carbon atoms, and alkenyl groups having up to 4 carbon atoms, comprising:

providing a solution of a non-racemic compound of the formula II:

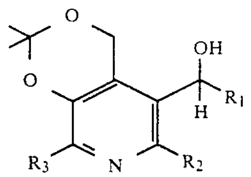

II wherein $R_1$, $R_2$, $R_3$ are as defined above; and adding concentrated strong acid to said solution in an amount sufficient to catalyze a deprotection/cyclodehydration reaction to yield compound I.

2. The method of claim 1 wherein said solution comprises compound II dissolved in a solvent that from an azeotrope with water.

3. The method of claim 2 wherein said solvent is selected form the group consisting of benzene, toluene, ethyl acetate and chloroform.

4. The method of claim 1 wherein said strong acid is selected from the group consisting of hydrochloric acid, sulfuric acid, perchloric acid and trifluoroacetic acid.

5. The method of claim 1, further comprising purifying compound II by alcohol or ethyl acetate crystallization before forming said solution.

6. The method of claim 1 further comprising the step of recovering said compound I from the reaction mixture.

7. The method of claim 6, wherein said recovery step comprises decanting excess solution comprising unreacted compound II from a residue produced by said cyclodehydration reaction, dissolving said residue in alcohol to produce a mixture, determining what part of said alcohol mixture is compound I, and isolating compound I from said alcohol mixture.

8. The method of claim 1, wherein the step of providing a solution of non-racemic compound II comprises:

dissolving the racemic achiral form of compound II in organic solvent to form a solution;

adding an oxidizing agent to said solution dropwise in an amount sufficient to completely react with all of the compound II racemate;

quenching the excess oxidizing agent with an alcohol;

cooling the liquid to produce a solid compound precipitate;

dissolving said solid crystals in tetrahydrofuran to form a mixture;

adding to said mixture a chiral reducing agent to reduce said solid compound to the desired chiral compound II; and isolating compound II and dissolving it in a solvent.

9. The method of claim 8 wherein said organic solvent is acetone, said oxidizing agent is Jones Reagent, said alcohol is isopropanol and said chiral reducing agent is lithium hydride (9-BBN-nopolbenzyl ether adduct).

10. The method of claim 1, wherein the step of providing a solution of non-racemic compound II comprises:

dissolving a compound of the formula III:

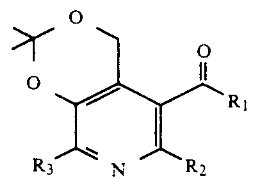

III wherein $R_1$, $R_2$ and $R_3$ are as defined above, in a vigorously stirred fermenting slurry of yeast, water and a carbohydrate;

adding additional carbohydrate and yeast to provide continued vigorous fermentation to form the desired chiral compound II;

continuing said fermentation until formation of compound II ceases; and isolating compound II and dissolving it in a solvent.

* * * * *

UNITED STATES PATENT AND TRADEMARK OFFICE
CERTIFICATE OF CORRECTION

PATENT NO. : 5,043,448
DATED : August 27, 1991
INVENTOR(S) : Charles Eck

It is certified that error appears in the above-identified patent and that said Letters Patent are hereby corrected as shown below:

Column 7, line 40, change "groups" to --group--.

Column 8, line 18, change "from" to --forms--.

Column 8, line 21, change "form" to --from--.

Signed and Sealed this

Twenty-sixth Day of January, 1993

*Attest:*

STEPHEN G. KUNIN

*Attesting Officer*

*Acting Commissioner of Patents and Trademarks*